US00PP21977P2

(12) United States Plant Patent
Dean et al.

(10) Patent No.: US PP21,977 P2
(45) Date of Patent: Jun. 14, 2011

(54) ***PHORMIUM* PLANT NAMED 'CHOCOMINT'**

(50) Latin Name: ***Phormium cookianum*×*Phormium tenax***
Varietal Denomination: Chocomint

(76) Inventors: Mark Dean, Oropi (NZ); Esme Dean, Oropi (NZ)

( * ) Notice: Subject to any disclaimer, the term of this patent is extended or adjusted under 35 U.S.C. 154(b) by 0 days.

(21) Appl. No.: 12/661,426

(22) Filed: Mar. 17, 2010

(51) Int. Cl.
*A01H 5/00* (2006.01)

(52) U.S. Cl. ..... Plt./373

(58) Field of Classification Search ..... Plt./373
See application file for complete search history.

(56) References Cited

OTHER PUBLICATIONS

Upov Plant Variety Database 2010/06. p 1.*

* cited by examiner

*Primary Examiner* — Annette H Para
(74) *Attorney, Agent, or Firm* — Penny J. Aguirre

(57) ABSTRACT

A new cultivar of hybrid *Phormium* named 'Chocomint' that is characterized by its foliage that is variegated with purple-brown centers and wide bright green margins, its stiff leaves, and its slightly arching plant habit.

2 Drawing Sheets

Botanical classification: *Phormium cookianum*×*Phormium tenax*.

Cultivar designation: 'Chocomint'.

CROSS REFERENCE TO A RELATED APPLICATION

This application is co-pending with a U.S. Plant Patent Application filed for a plant derived from similar parentage in the Inventors' breeding program that is entitled *Phormium* Plant Named 'Moonraker' (U.S. Plant patent application Ser. No. 12/661,442).

BACKGROUND OF THE INVENTION

The present invention relates to a new and distinct cultivar of *Phormium* named 'Chocomint', an interspecific hybrid of *Phormium cookianum*×*Phormium tenax* and referred to hereafter by its cultivar name, 'Chocomint'. The new cultivar is grown for use as a foliage plant for landscape and container use.

The Inventors discovered the new cultivar summer of 2000 as a naturally occurring chimeral mutation of *Phormium* 'Yellow Wave' (not patented) in a container block in their nursery in Tauranga, New Zealand.

Asexual reproduction of the new cultivar was first accomplished by division in autumn of 2000 in Tauranga, New Zealand by one of the Inventors. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Chocomint' as a new and unique cultivar of *Phormium*.

1. 'Chocomint' exhibits foliage that is variegated with purple-brown centers and wide bright green margins.

2. 'Chocomint' exhibits stiff leaves with a slightly arching plant habit.

'Chocomint' can be compared to the parent plant, 'Yellow Wave'. 'Yellow Wave' differs from 'Chocomint' in having foliage with variegation that is yellow, green, and cream in color and in having leaves that are less stiff. The closest comparison cultivars are 'Co-ordination' and 'Sea Jade' (both unpatented) as they are similar in having leaves with green and brown variegation. 'Co-ordination' differs from 'Chocomint' in having narrower leaves, a more upright habit, and in having leaves with lighter bronzy brown centers rather than the darker purple-brown of 'Chocomint'. 'Sea Jade' differs from 'Chocomint' in having leaves that are wider with lighter green margins and bronzy brown centers, and in having a strongly upright and taller plant habit.

BRIEF DESCRIPTION OF THE DRAWING

The accompanying colored photographs illustrate the overall appearance and distinct characteristics of the new *Phormium*.

The photographs in FIG. 1 and FIG. 2 were taken of a two year-old plant of 'Chocomint' as grown outdoors in a 3-liter container in Auckland, New Zealand.

DETAILED BOTANICAL DESCRIPTION OF THE PLANT

Figure 1:
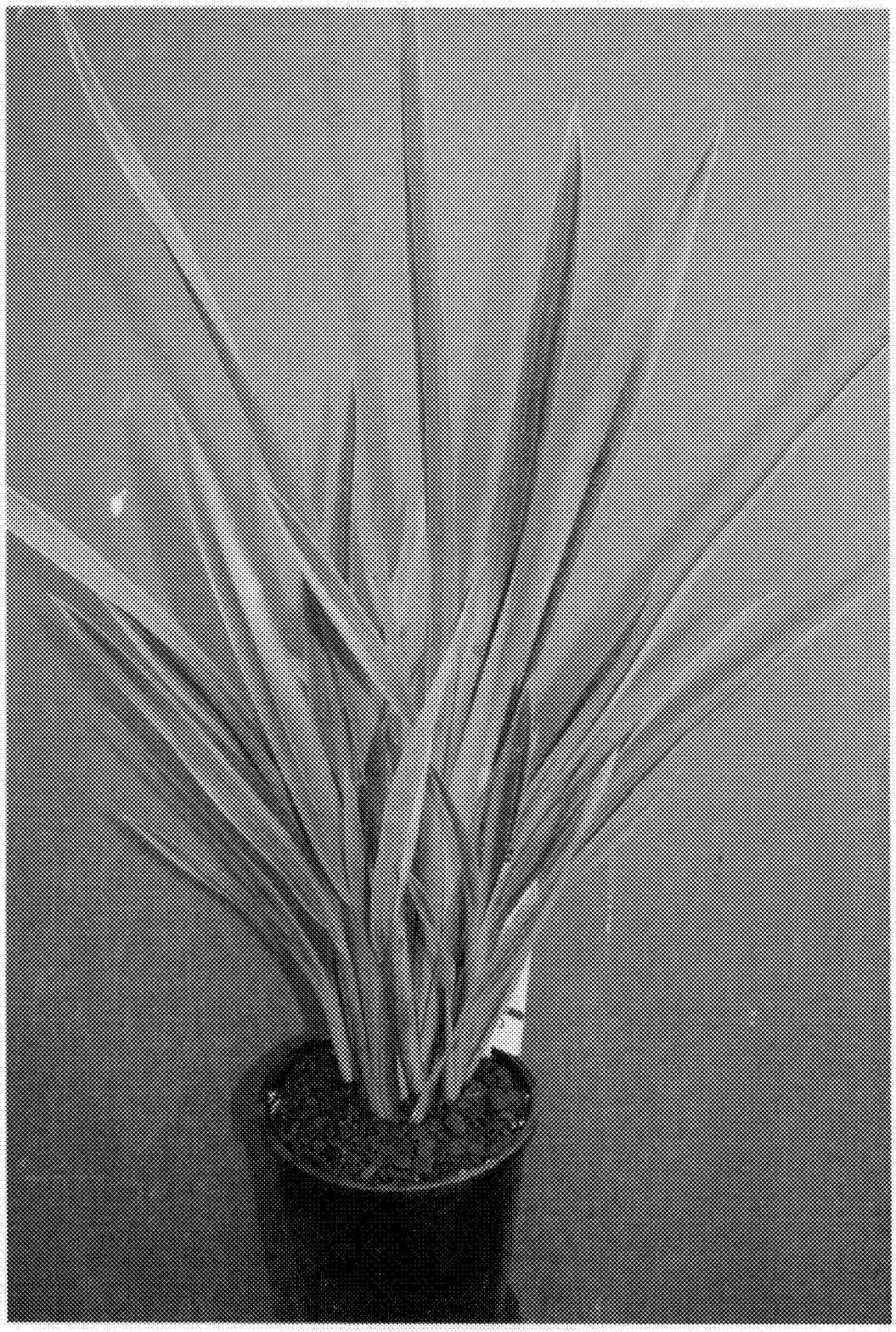
FIG. 1 provides a side view of 'Chocomint'.
Figure 2:
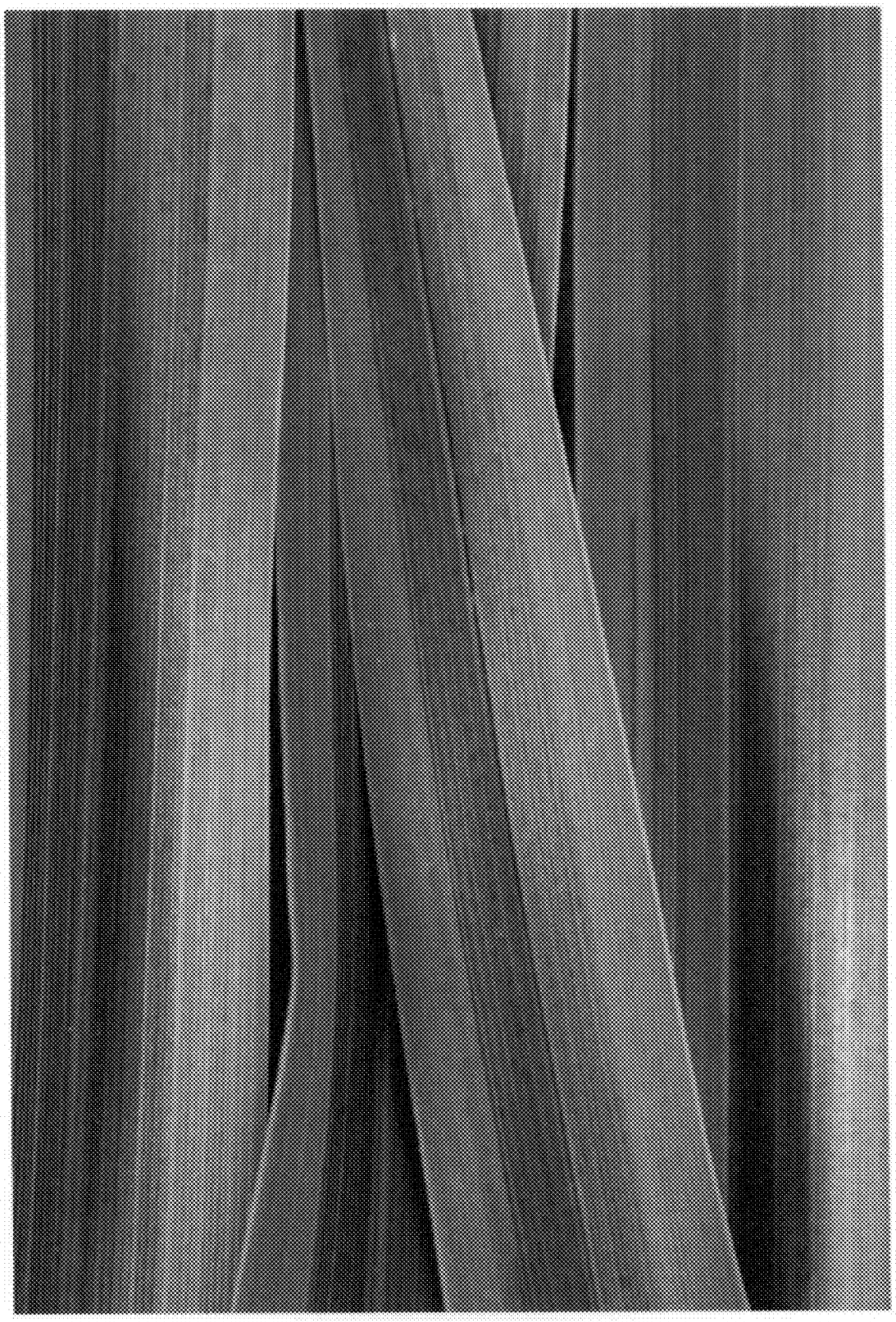
FIG. 2 provides a close up view of the foliage of 'Chocomint'. The colors in the photographs may differ slightly from the color values cited in the detailed botanical description, which accurately describe the colors of the new *Phormium*.

The following is a detailed description of two year-old plants of the new cultivar as grown outdoors in 3-liter containers in Auckland, New Zealand. The plants were grown under average day temperatures of 20 to 27° C. and average night temperatures of 12 to 20° C. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Blooming period.*—No flower production has been observed.

*Plant type.*—Perennial, evergreen.

*Plant habit.*—Clump-forming, emerge upright and become arching.

*Height and spread.*—Reaches 60 to 70 cm in height and 70 to 80 cm in width when in the landscape.

*Hardiness.*—U.S.D.A. Zones 9a to 10b, tolerant to high temperatures of 40° C. and low temperatures of −5° C.

*Diseases and pests.*—No unique susceptibility or resistance to diseases or pests has been observed.

*Root description.*—Fibrous with some larger fleshy roots, 2 to 4 mm in diameter, vigorous, 8D in color.

*Propagation.*—Division.

*Growth rate.*—Moderate relative to *Phormium*, produces 4 to 6 fans per 3-liter container.

*Root development.*—Divisions take 6 to 8 weeks to develop new roots when grown at 20° C.

*Stem description.*—Stem-less, leaves are equitant from base.

Foliage description:

*Leaf shape.*—Lanceolate.

*Leaf division.*—Simple.

*Leaf base.*—Sheathed, overlapping.

*Leaf apex.*—Acuminate.

*Leaf venation.*—Parallel, not prominent, same color as leaves, mid rib protruding sharply on lower surface (keel).

*Leaf margins.*—Entire.

*Leaf attachment.*—Sheathed, lacks petioles.

*Leaf arrangement.*—Equitant.

*Leaf number.*—Average of 30 as grown in a 3-liter container.

*Leaf orientation.*—Held upright and becomes arching, moderately to deeply concave with sharp keel.

*Leaf substance.*—Thick, stiff, leathery, durable.

*Leaf surface.*—Smooth with fine longitudinal lines, upper surface satiny, lower surface slightly glaucous.

*Leaf color.*—Young and mature leaves upper surface; centers: a blend of 79A and 200A with a occasional thin lines of 146A, margins: 146A and 146B (fine longitudinal lines of each).

*Leaf size.*—50 to 70 cm in length and 4 to 6 cm in width.

It is claimed:

1. A new and distinct cultivar of *Phormium* plant named 'Chocomint' as herein illustrated and described.

* * * * *